(12) United States Patent
Takeuchi (10) Patent No.: US 6,486,952 B2
(45) Date of Patent: Nov. 26, 2002

(54) SEMICONDUCTOR TEST APPARATUS

(75) Inventor: Nobuaki Takeuchi, Tokyo (JP)

(73) Assignee: Ando Electric Co., Ltd., Tokyo (JP)

( * ) Notice: Subject to any disclaimer, the term of this patent is extended or adjusted under 35 U.S.C. 154(b) by 13 days.

(21) Appl. No.: 09/864,678

(22) Filed: May 24, 2001

(65) Prior Publication Data

US 2001/0048527 A1 Dec. 6, 2001

(30) Foreign Application Priority Data

May 31, 2000 (JP) ........................................ 2000-163512

(51) Int. Cl.[7] .................................................. G01J 4/00
(52) U.S. Cl. ................................... 356/369; 356/237.2
(58) Field of Search ................................. 356/364, 369, 356/606, 607, 237.2, 237.3, 237.4, 237.5; 250/550, 559.01

(56) References Cited

U.S. PATENT DOCUMENTS 5,546,181 A * 8/1996 Kobayashi et al. ......... 250/550
5,726,756 A * 3/1998 Aki et al. .............. 250/559.27

* cited by examiner

*Primary Examiner*—Mark A. Robinson
(74) *Attorney, Agent, or Firm*—Darby & Darby (57) ABSTRACT

In the present invention, measuring the one-dimensional or two-dimensional voltage distribution or electrical field distribution in a measured device is made possible, and a reduction in the measuring time can be implemented. The present invention comprises a first optical system (2, 3) wherein light emitted from the light source is shaped into a line-shaped light beam and irradiates a desired measurement line in the measured device via the electrooptic element, a second optical system (7, 8, 9) that maintains as-is the shape of the line-shaped light beam reflected from the desired measurement line in the measured device after transiting the electro-optic element, a light receiving device (10) that receives the line-shaped light beam emitted from the second optical system and converts each of the measured points to an electrical signal depending on the strength of each light beam reflected at each of the measured points on the desired measurement line on the measured device and outputs the result, and a signal processing device (11, 12, 13, 14, 16) that calculates the voltage or electrical field at each of the measured points of the measured device from the output signal of the light receiving device and calculates the electrical field distribution or the voltage distribution at the measured part of measured device.

11 Claims, 7 Drawing Sheets

SEMICONDUCTOR TEST APPARATUS

BACKGROUND OF THE INVENTION

1. Field of the Invention

The present invention is related to a semiconductor device, and in particular to a semiconductor testing device that measures the electrical field distribution or the voltage distribution or each measured point during testing of a device under test (DUT).

2. Description of Related Art

Figure 7:
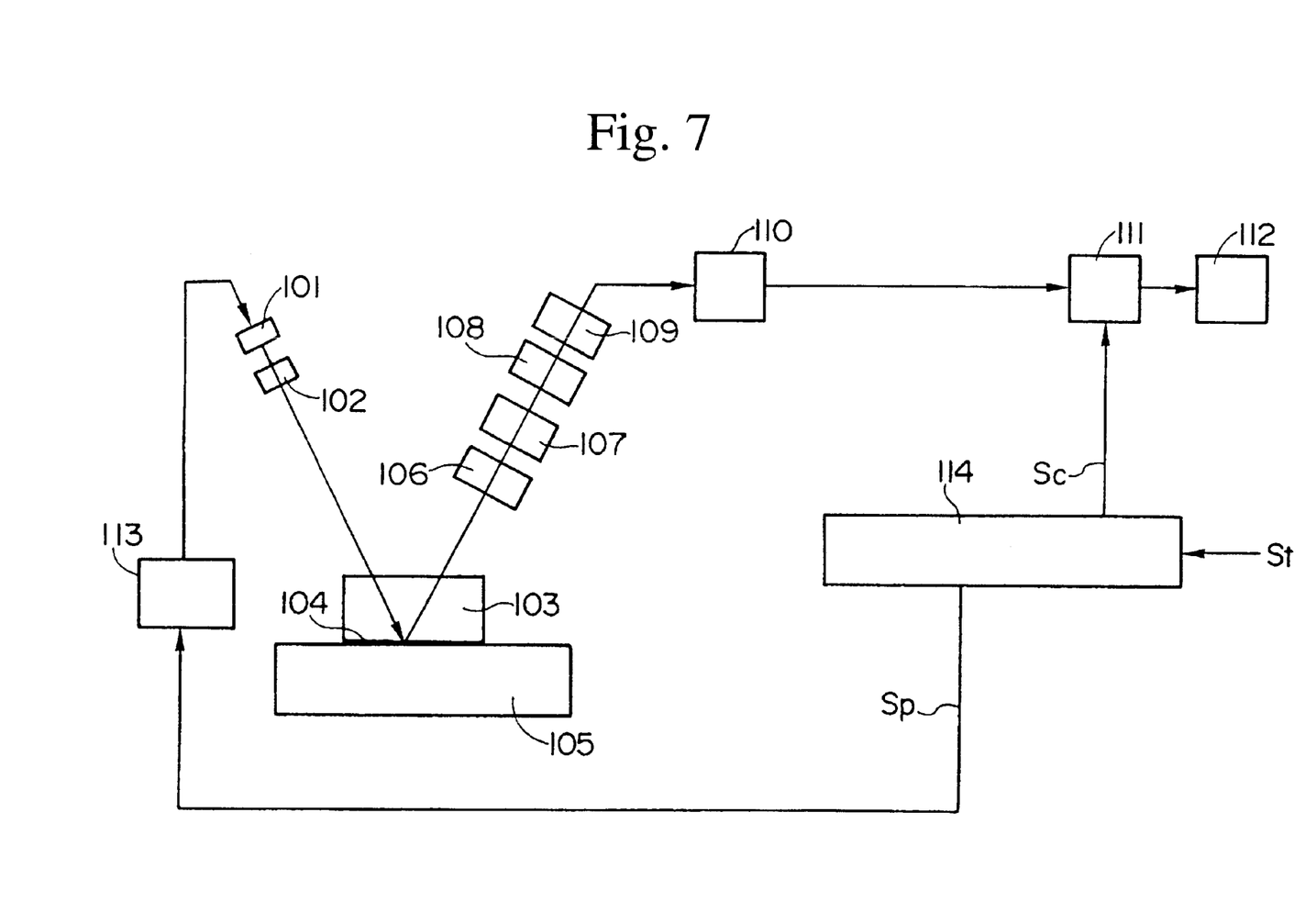
FIG. 7 is a block diagram showing an example of the structure of a conventional semiconductor test apparatus.

An example of conventional technology for this type of semiconductor testing apparatus is described in a paper by Shinagawa et al., "Handy-type high impedance probe using an EOS," The 15th Light Wave Technology Research Conference, 1995, pp. 123–129. In addition, the structure of another conventional semiconductor test apparatus is shown in FIG. 7. In this figure, the semiconductor test apparatus has a light source 101, and a pulsed laser is emitted under control of the light source drive circuit 113. The light pulse emitted by the light source 101 is condensed by the condenser lens 102, and condensed onto the electrooptic element 103.

The electrical field generated by the voltage input into and output from each pin of the DUT 105 is also present in the electrooptic element 103. While the light pulse condensed by the condenser lens 102 transits the electrooptic element 103, the polarization thereof changes (modulates) due to the electrical field generated by the measured device 105.

This light pulse is reflected by the reflecting plate 104 provided on the lower surface of the electrooptic element 103, and after transiting the wavelength plate 106 and the analyzer 107, this light is condensed on the electrooptic converter 109 by the condenser lens 108. The analyzer 107 has the property of changing the polarity component of the light to an intensity component, and the signal component of the light polarized by the electrooptic element 103 is converted to an intensity signal (amplitude information) due to transiting the analyzer 107.

The optoelectric converter 109 converts the intensity (amplitude) of the light to the intensity (amplitude) of the electric signal. The electrical field generated by the voltage signal in each of the pins of the measured device 105 is made proportional to the level of the voltage signal, and thereby the amplitude of the electric signal generated in the optoelectric converter 109 is made proportional to the voltage in the measured device 105. This electric signal is amplified by the amplifying circuit 110, and converted to a digital signal by the A/D converting circuit 111.

The trigger signal St is a trigger signal that represents the measurement from the measured device and the like. Based on the A/D conversion timing signal Sc output from the timing generation circuit 114 in synchronicity with this signal, the measurement data of the measured device 105 is input by the A/D conversion circuit 111, A/D converted, and the electrical field and the voltage value are calculated and displayed by the calculation/display circuit 112.

Figure 8:
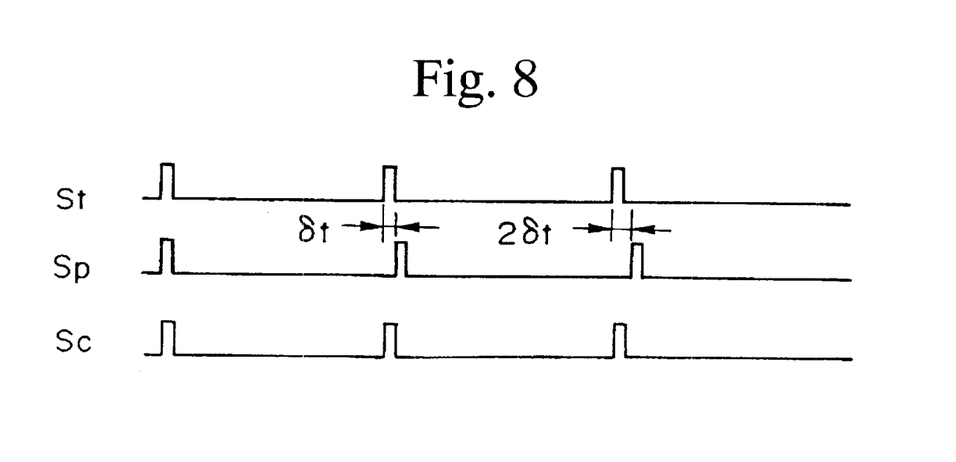
FIG. 8 is a timing chart showing the operation timing for each part of the conventional semiconductor test apparatus shown in FIG. 7.

The timing operation of the semiconductor apparatus shown in FIG. 7 is shown in FIG. 8. As shown in this figure, in the case that the light source 101 emits a continuous light, at the timing represented by the AID conversion timing signal Sc, in sequence, the data is input into the A/D conversion circuit 111, A/D converted, and the digital data that has been A/D converted is sent to the calculation/display circuit 112. In this case, the output timing of the trigger signal St serves as the data input commencement timing.

Next, in the case that the light source emits a pulsed light, each time the trigger signal St is input, the pulsed emitted light timing signal Sp from the timing generation circuit 114 is output such that each time the phase is delayed by δt, and the light pulse is emitted from the light source 101 by controlling the drive of the light source drive circuit 113 by the pulsed light emission light timing signal Sp.

In the A/D conversion circuit 111, data is input by the A/D conversion timing output from the timing generating circuit 114, A/D conversion is carried out, and the digital data that has been A/D converted is sent to the calculation/display circuit 112.

In the case that the light source 101 is driven so as to emit pulsed light, the measuring signal of the measured device 105 requires a return signal synchronized with the trigger signal 23. This method is an existing technology called sequential sampling.

In the calculation/display circuit 112, the digital data obtained by the A/D conversion circuit 111 is multiplied by the sensitivity of the measurement system, converted to a voltage or electrical field at the measurement point of the measured device 105, and displayed as a data value, waveform, or a time series.

The conventional technology for the semiconductor test apparatus described above is disclosed in Japanese Patent Application, No. Hei 09-273156. In addition, similar functions for the light source 101, condensing lens 102, the electrooptic element 103, reflecting plate 104, wavelength plate 106, analyzer 107, condenser lens 108, and the optoelectric conversion 109 are disclosed in this publication.

In the above-described EOS (Electro-Optic Sampling)-type semiconductor test apparatus, measurement of only one point on the measured device is possible, and for example, there is the problem that even in the case that the pins of the integrated circuit are arranged in a row, they must be measured by moving the irradiating position of the light beam emitted from the light source for each pin in sequence, and much time must be consumed.

Furthermore, in the case that the distribution of the voltage of electrical field of the entire measured device is measured, there are the problems that the light beam must be swept in two dimensions relative to the measured point, and due to measuring by sweeping the light beam in two dimensions, the system structure becomes complicated, and the measuring time becomes long.

In addition, in the above-described EOS-type semiconductor test apparatus, in the case that a plurality of measured points are to be measured, measurement must be conducted by moving the light beam in sequence, and thus in the case that many points in the measured device are measured simultaneously (at the same time), there is the problem that a plurality of sensors is necessary.

SUMMARY OF THE INVENTION

In light of the above-described circumstances, it is an object of the present invention to provide a semiconductor test apparatus that can measure the voltage distribution and the electrical field distribution of the measured device in one or two dimensions, and can implement a reduction in the measuring time.

In order to attain the above objectives, in a semiconductor test apparatus wherein a light beam emitted from a light source irradiates a measured part of a measured device via an electrooptic element arranged above the measured device and the electrical field distribution or the voltage distribution in the measured part of the measured device is calculated by electrically detecting the change in the state of the polarization of this reflected beam, a first aspect of the invention is characterized in comprising a first optical system wherein light emitted from the light source is shaped into a line-shaped light beam and irradiates a desired measurement line on the measured device via the electrooptic element, a second optical system that maintains as-is the shape of the line-shaped light beam reflected from the desired measurement line on the measured device after transiting the electrooptic element, and modulates the change in polarity of the line-shaped light beam to a change in intensity of the light, a light receiving device that receives the line-shaped light beam emitted from the second optical system and converts the light beam at each of the measured points to an electrical signal depending on the strength of each light beam reflected at each of the measured points on the desired measurement line on the measured device and outputs the result, and a signal processing device that calculates the voltage or electrical field at each of the measured points of the measured device from the output signal of the light receiving device and calculates the electrical field distribution or the voltage distribution at the measured part of measured device.

In addition, in a second aspect of the invention, in the semiconductor test apparatus according to the first aspect, the signal processing device is characterized in comprising a sample holding circuit that holds samples of the output signal of the light receiving device simultaneously for each of the measured points of the measured device, a selection circuit that selects in sequence the samples of the signals held by the sample holding circuit, an A/D conversion circuit that A/D converts the analog signal selected by the selecting circuit, and a timing generation circuit that outputs a timing signal that controls the operating timing of the sample holding circuit, the selection circuit, and the A/D conversion circuit.

In addition, in a third aspect of the invention, in the semiconductor test apparatus according to the first aspect, the first optical system comprises a condenser lens that condenses the light emitted from the light source, and a curved mirror that shapes the light beam condensed by the condenser lens into a line-shaped light beam and irradiates a desired measurement line on the measured device via an electrooptic element.

In addition, in a fourth aspect of the invention, in the semiconductor test apparatus according to the first aspect, the second optical system comprises a reflecting plate that is arranged on the lower surface of the electrooptic element, and reflects the line-shaped light beam irradiated by the first optical system, a wavelength plate that converts the line-shaped light beam reflected by the reflecting plate to line-shaped polarized light, an analyzer that converts an amount of polarization of the line-shaped light beam that has transited the wavelength plate to an amount of amplitude, and a microlens array that condenses each of the reflected light beams corresponding to each of the measured points of the measured device on the line-shaped light beam that has transited the analyzer on each of the light receiving surfaces of the light receiving device corresponding to each of the reflected light beams.

In addition, in a fifth aspect of the invention, in the semiconductor test apparatus according to the first aspect, the semiconductor test apparatus further comprises a calculation/display device, and this calculation/display device calculates and displays the electrical field or the voltage value based on the output signals of the A/D converting circuit.

In addition, in a sixth aspect of the invention, in the semiconductor test apparatus according to any of the first through fifth aspects, the calculation/display device displays the electrical distribution or the voltage distribution on the measurement line of the measured device that has been obtained based on the amplitude information of the reflected beam of the line-shaped light beam irradiating the measured device via the electrooptic element.

In addition, in a seventh aspect of the invention, in a semiconductor test apparatus according to the fifth aspect, the signal processing means calculates a plurality of times the electrical field distribution or voltage distribution on the measurement line of the measured device obtained based on the amplitude information of the reflected beam of the desired line-shaped light beam that irradiates the measured part of the measured device, and the calculation/display device displays on a time axis the electrical field distribution or voltage distribution on the measurement line of the measured device that have been calculated a plurality of times.

In addition, in an eighth aspect of the invention, in a semiconductor test apparatus according to the first aspect, the light source is driven so as to emit light continuously, and at each timing wherein the A/D conversion of the signal representing the electrical field or voltage at each of the measured points of the measured part in the measured device irradiated by the line-shaped light beam has completed, the sample holding circuit holds samples of the signals representing the electrical field or voltage at each of the measured points.

In addition, in a ninth aspect of the invention, in a semiconductor test apparatus according to the first aspect, the timing is such the A/D conversion rate of the A/D converting device ADDed to the number of signals output from the light receiving device becomes equal to the sample rate of the sample holding circuit, and the light source is driven so as to emit pulsed light at a timing synchronous with a reference signal that determines the measurement timing, and at the same time, the sample holding circuit holds samples of the signals that represent the electrical field or the voltage of each of the measured points at the measured parts of the measured device irradiated by the line-shaped light beam at a timing in synchronism with the light emission timing.

In addition, in a tenth aspect of the invention, in a semiconductor test circuit according to the first aspect, the signal processing means is characterized in comprising a plurality of amplifying circuits that amplify each of the plurality of output signals output from the light receiving devices, a plurality of A/D conversion circuits that A/D convert each of the output signals of the plurality of amplifying circuits, a plurality of latch circuits that latch the output signals of the plurality of A/D conversion circuits, and a selection circuit that selects in sequence each of the outputs of the plurality of latch circuits.

In addition, in an eleventh aspect of the present invention, in the semiconductor test circuit according to the first aspect, the magnetic field distribution or the current distribution in the desired measured part of the measured device are calculated using a magneto-optic element instead of the electrooptic element.

According to the first aspect of the invention, in a semiconductor test apparatus wherein a light beam emitted from a light source irradiates a measured part of a measured device via an electrooptic element arranged above the measured device and the electrical field distribution or the voltage distribution in the measured part of the measured device is calculated by electrically detecting the change in the state of the polarization of this reflected beam, a first aspect of the invention is characterized in comprising a first optical system wherein light emitted from the light source is shaped into a line-shaped light beam and irradiates a desired measurement line in the measured device via the electrooptic element, a second optical system that maintains as-is the shape of the line-shaped light beam reflected from the desired measurement line in the measured device after transiting the electrooptic element, a light receiving device that receives the line-shaped light beam emitted from the second optical system and converts and outputs for each of the measured points to an electrical signal depending on the strength of each light beam reflected at each of the measured points on the desired measurement line on the measured device, and a signal processing device that calculates the voltage or electrical field at each of the measured points of the measured device from the output signal of the light receiving device and calculates the electrical field distribution or the voltage distribution at the measured part of measured device, and thereby the one-dimensional or two-dimensional voltage distribution or electrical field distribution in a measured device can be calculated, and a reduction of the calculating time can be implemented.

In addition, according to the eleventh aspect of the invention, in the semiconductor test circuit according to the first aspect, the magnetic field distribution and the current distribution in the desired measured part of the measured device are calculated using a magneto-optic element instead of the electrooptic element, and thereby voltage distribution or electrical field distribution in a measured device can be calculated in one-dimension or two-dimensions, and thereby a reduction of the calculating time can be implemented.

DETAILED DESCRIPTION OF THE INVENTION

Figure 1:
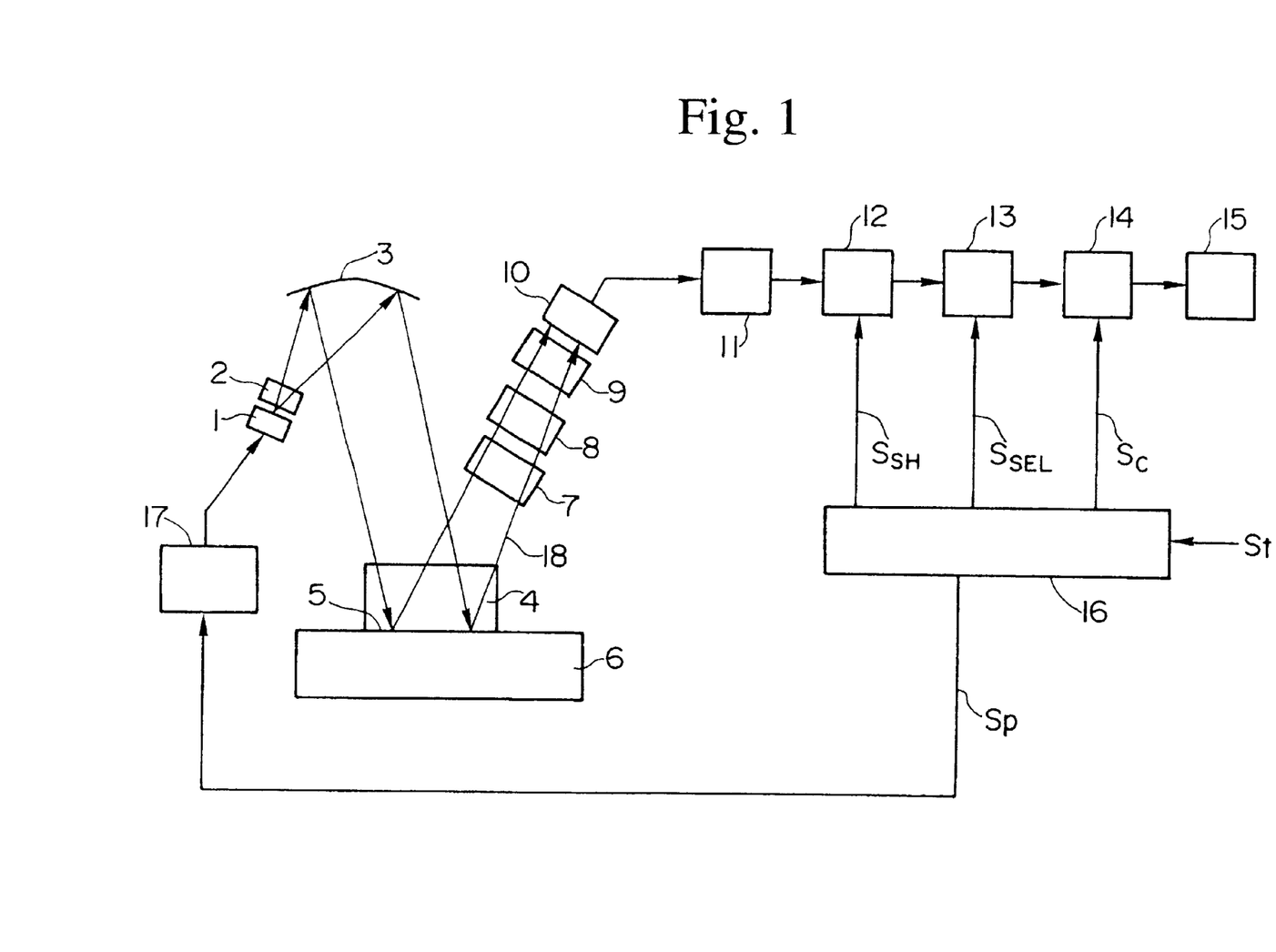
FIG. 1 is a block drawing showing the structure of the semiconductor test apparatus according to an embodiment of the present invention.

Below, an embodiment of the present invention will be explained referring to the figures. The structure of the semiconductor test apparatus according to the embodiment of the present invention is shown in FIG. 1. In this figure, the semiconductor test apparatus according to the present invention comprises a light source 1, a condenser lens 2 that condenses the light that is emitted from the light source, and a curved mirror 3 that shapes the light beam transiting the condenser lens 2 to a straight light beam in the widthwise direction perpendicular to the direction of the progress of the beam. Light source 1, the condenser lens 2, and the curved mirror 3 correspond to the first optical system of the present invention.

In addition, the semiconductor test apparatus according to this embodiment of the present invention comprises an electrooptic element 4 disposed on top of the measured part of the measured device 6, a reflecting plate 5 that is disposed under the electrooptic element 4 and reflects the straight light beam reflected by the curved mirror 3, a wavelength plate 7 converts the straight light beam into straight polarized light, an analyzer 8 that converts the amount of polarization of the straight light beam that transits the wavelength plate 7 to an amount of amplitude, microlens array 9 that condenses each reflected light beam corresponding to each measured point of the measured device 6 in the straight light beam that has transited the analyzer 8 onto each light receiving surface of the line sensor 10 corresponding to each of the reflected light beams, and a line sensor 10 serving as a light receiving device. The line array 10 receives the straight light beam via the microlens array 9, for each measured point converts it to an electrical signal corresponding to the strength of each light beam reflected at each of the measured points on the desired measurement line on the measured device 6, and outputs it. The reflecting plate 5, the wavelength plate 7, and analyzer 8, and the microlens array 9 correspond to the second optical system of the present invention.

Furthermore, the semiconductor test apparatus according to the embodiment of the present invention comprises an amplifying circuit 11 that amplifies the output signal of the line sensor 10, a sample hold circuit 12 that simultaneously holds each samples of the output signal of the amplifying circuit 11 for each measured point on the desired measurement line in the measured device 6, a selecting circuit 13 that selects in sequence a signal being held as samples by the sample hold circuit 12, an A/D conversion circuit 14 that A/D converts the analog signal selected by the selecting circuit 13, a calculating/display circuit 15 that calculates and displays the electrical field or the voltage value based on the output signal of the A/D conversion circuit 14, a light source driving circuit 17 that drives the light source 1, and a timing generating circuit 16 that outputs a timing signal that controls the timing of the operation of the sample holding circuit 12, the selection circuit 13, the A/D conversion circuit 14, and the light source drive circuit 17. The amplification circuit 11, the sample holding circuit 12, the selecting circuit 13, the A/D conversion circuit 14, and the timing generating circuit 16 constitute the signal processing device of the present invention.

In the structure described above, the light source 1 emits a laser light by driving the light source drive circuit 17. The laser light emitted from the light source 1 is condensed by the condenser lens 2 and guided to the curved mirror 3. At the curved mirror 3, the light beam that has transited the condenser lens 2 is shaped into a straight light beam in the width direction perpendicular to the direction of progress of this beam. After the laser beam reflected by the curved mirror 3 irradiates the electrooptic element 4 and is reflected by the reflecting plate 5, it transits the analyzer 8, is condensed by the microlens array 9, and input into the line sensor 10. The light path 18 schematically shows the path of the laser light.

Figure 3A:
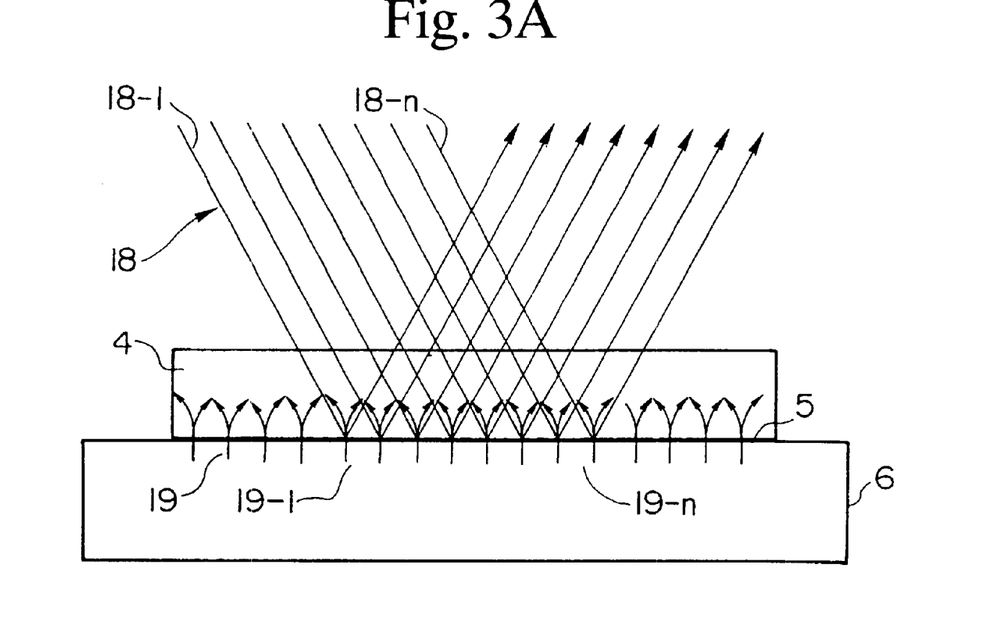
FIGS. 3A and 3B are respectively a top view and a side view of the electrooptic element showing the condition when the light beam from the light source is input or emitted in the semiconductor test apparatus according to the embodiment of the present invention shown in FIG. 1.
Figure 3B:
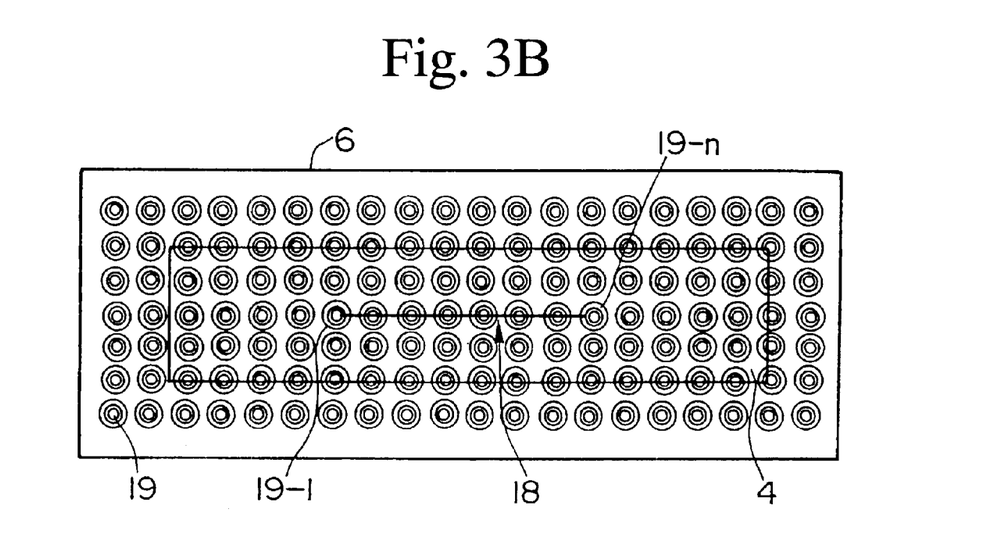

A side view of the electrooptic element 4 is shown in FIG. 3A, and a view from the top of the same is shown in FIG. 3B. At the border between the surfaces of the electrooptic element 4 and the reflecting plate 5, as shown in FIG. 3B, the first optical system comprising the light source 1, the condenser lens 2, and the curved mirror 3 is disposed such that in the upper part of the figure of the electrooptic element 4, the laser light irradiates in substantially a straight line, as is schematically represented as the light path 18. Specifically, the curved mirror 3 is a columnar mirror having an arc or a parabolic surface arc, and the cross-section of the reflected light can possess optical properties such as a straight-line shape or an elongated ellipse shape.

Furthermore, in the case that the light source uses a laser diode, generally the light emitting surface of the laser diode has an elliptical shape, and thus the lengthwise axis direction can be disposed so as to coincide with the columnar direction of the curved mirror 3.

The microlens 9 and a line sensor 10 are disposed such that the laser light reflected by the reflecting plate 5 is condensed by the microlens array 9, and input into the line sensor 10 at the light receiving surface (light receiving line). In order to attain this, disposition must be carried out taking into consideration not only the microlens 9 and the line sensor 10, but also the light source 1, the condenser lens 2, the curved mirror 3, and electrooptic element 4, and the reflecting plate 5.

The microlens 9 is a complex lens having a plurality of lenses arranged in a straight line, and is formed such that a laser beam whose cross-section has a line-shaped or elongated oval shape can transit the lens.

The microlens array 9 is structured such that the sample holding circuit 12 does not form a straight line but a surface. However, in this situation, the reflected light beam does not transit the entirety of the lens surface from the reflecting plate 5, but transits only a part thereof. The laser light is partitioned into a plurality of beams by transiting the reflected beam microlens array 9, and each of the light beams irradiate each of the light receiving surfaces coinciding with the line sensor 10.

The change in voltage emitted by the measured device 6 is also present in the electrooptic element 4 as a change in the electrical field. The polarity of the laser beam emitted from the light source that transits the electrooptic element 4 undergoes a change due to this electrical field. Here, because the cross-section of the laser beam has a line-shape or an elongated elliptical shape, the amount of the change in polarization due to this electrical field differs depending on the position. This will be explained referring to FIGS. 3A and 3B. In these figures, the light paths 18 schematically show the light paths of the laser beam, and shows schematically that these light paths are one-dimensional (line-shaped) from the light path 1 to light path n. The incident light transits a different location on the electrooptic element 4 from the light path 18-1 to light path 18-n.

From the measured device 6, the electrical field 19 radiates to the electrooptic element 4, and the laser light of the light path 18-1 transits the electrical field 19-1. Similarly, the light path 18-n transits up to the electrical field 19-n. The laser light of the light path 18-1 is subject to a change in polarization at the electrical field 19-1, and the laser light of light paths 18-2, 18-3, . . . , 18-n are subject to change in polarization at the respective electrical fields 19-2, 19-3, . . . , 19-n.

The analyzer 8 has the property of transforming the amount of polarization of the light into an amount of amplitude, and at the electrooptic element 4, the laser light having the changed polarization undergoes a change in amplitude by transiting the analyzer 8.

In this manner, the amount of change in the voltage depending on the position of the measured device 6 becomes an amount of change in amplitude depending on the position of the laser light, the light transits the microlens array 9, and is converted by a change in the amplitude of the electric signal by the line sensor 10. Due to this, the output electric signal of the line sensor 10 can become an electric signal that is proportional to the electrical field or the voltage of each position of the measured device 6.

The output signal of the line sensor 10 is amplified by the amplifying circuit 11, and a sample thereof is held by the sample holding circuit 12. One of the plurality of signals of the output signal of the sample holding circuit 12 is selected by the selecting circuit 13, is converted into a digital signal by the A/D converting circuit 14, and input into the calculating/display circuit 15. Here, the amplifying circuit 11 and the sample holding circuit 12 are provided in a plurality corresponding to the plurality of outputs corresponding to the plurality of light receiving surfaces of the line sensor 10, and structured such that the plurality of output signals of the line sensor 10 are amplified in parallel and samples are held.

Figure 2A:
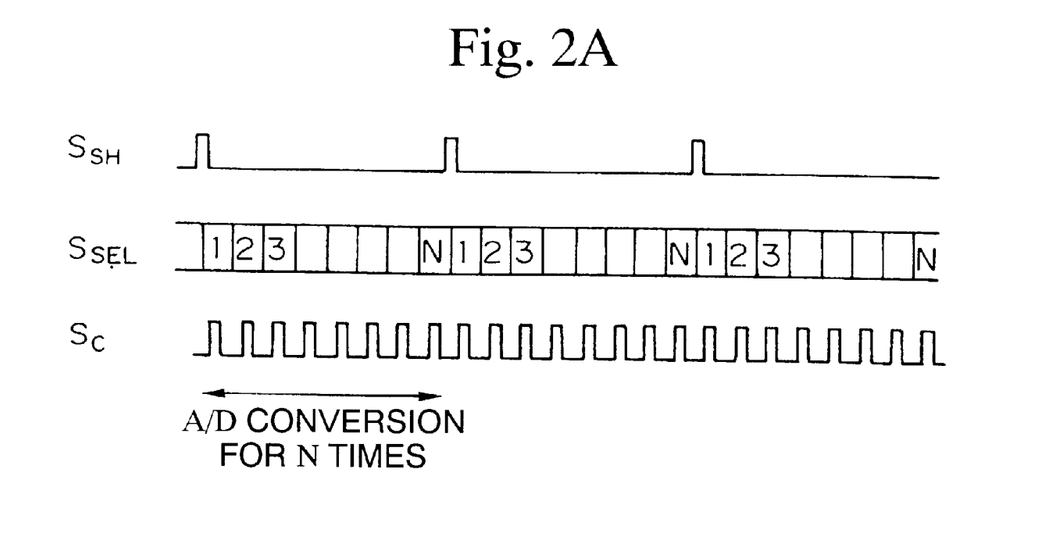
FIGS. 2A and 2B are timing charts showing the timing operation for each part in the signal processing device in the semiconductor test apparatus according to the embodiment of the present invention shown in FIG. 1.
Figure 2B:
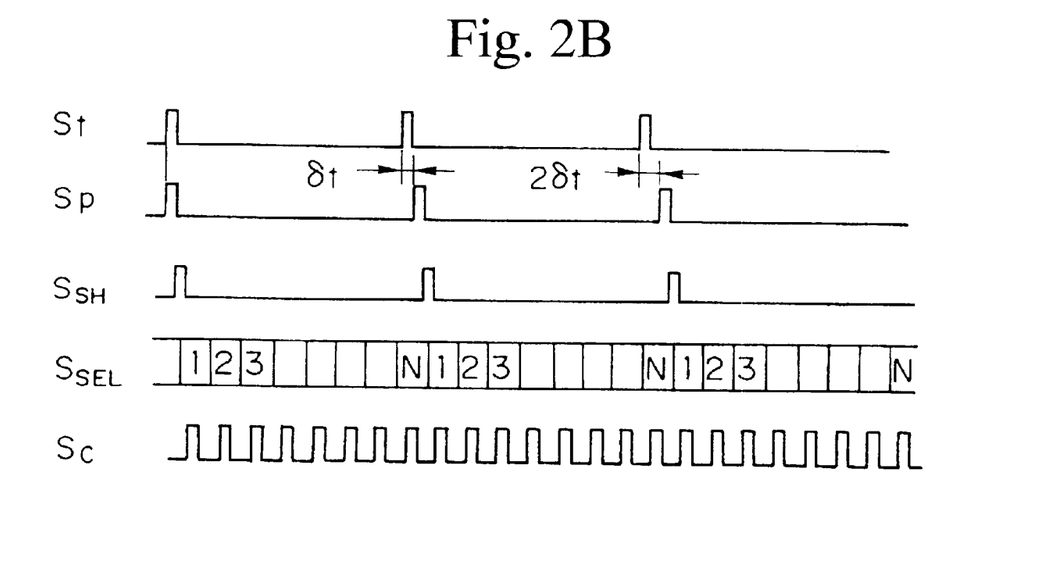

The operation of the semiconductor test apparatus shown in FIG. 1 will be explained referring to the timing circuit in FIG. 2. FIG. 2A shows the timing signal in the case that the light source 1 has a continuous emission, and FIG. 2B shows the timing signal in the case that the light source 1 is a pulsed emission. Moreover, in the present invention, the essential character of the light source 1 does not change for a continuous light emission or a pulsed light emission. In the case that the light source 1 has a continuous light emission, samples of all of the output signals of the amplifying circuit 11 are held in synchronism with the sample hold timing signal $S_{SH}$ output from the timing generating circuit 16 (this signal is output at the timing of the completion of the A/D conversion at each measurement point of the measured part of the measured device 6). Thereby, samples of the signals of each measured point in the desired measurement line in the measured device 6 are held simultaneously. The outputs (1 to N) of the sample holding circuit 12 are selected in sequence by the output timing of the selecting circuit timing signal $S_{SEL}$ output from the timing generating circuit 16 at the selection circuit 13.

The A/D conversion circuit 14 A/D converts the signals selected by this selection circuit 13 in sequence in synchronism with the A/D conversion timing signal Sc output from the timing generating circuit 16. This means that samples of N signals held one time are divided in order N times, and A/D converted.

Next, the case in which the light source 1 is a pulsed emission will be explained. In the case that the light source 1 is driven by the light source driving circuit 17 so as perform pulsed emission, the measurement signal obtained from the measured part in the measured device 6, that is, the output signal of the line sensor 10, must be a return signal in synchronism with the trigger signal 23.

Each time the trigger signal St is input, the pulsed light emission timing signal $S_p$ is generated by the timing generating circuit 16 so as to be delayed each time by δt, and a light pulse is emitted from the light source 1.

The samples of the measuring signal of the electrical field or the voltage of each measured point in the measurement line of the measured device 6 obtained by this light pulse being irradiated towards the reflection plate 5 disposed on the surface of the measured device via the curved mirror 3 and the electrooptic element 4 are held simultaneously in synchronism with the sample hold timing signal $S_{SH}$ from the sample holding circuit 12. This means in the case that the light source 1 emits pulsed light, the A/D conversion rate of the A/D conversion circuit 14 ADDed to the number of signals output from the line sensor 10 that is acting as a light receiving means yields a timing that becomes equal to the sample rate of the sample holding circuit 12, and is driven such that the light source 1 performs pulsed light emission at a timing in synchronism with the trigger signal St, which is a reference signal that is regulated by the measurement timing. At the same time, the sample hold circuit 12, at a timing in synchronism with this light emission timing carries out holding of a sample of the signal representing the electrical field or the voltage of each measured point in the measured part of the measured device 6 that the line-shaped light beam irradiates.

The outputs (1 to N) of the sample holding circuit 12 are selected by the selection circuit 13 in sequence in synchronism with the selection circuit timing signal $S_{SEL}$. In the A/D conversion circuit 14, the signal selected by the selection circuit 13 are A/D converted in sequence in synchronism with the AID conversion timing Sc. That is, the samples of N signals that are held once are divided and A/D converted N times. By repeating this operation, digital data can be obtained that serves as the measurement signal of the electrical field or voltage on the measurement line of the measured device 6.

The calculation/display circuit 15 displays the electrical field distribution or the voltage distribution on the measurement line of the measured device 6 that is obtained based on the amplitude information of the reflected beam with respect to the line-shaped light beam irradiated via the electrooptic element 4 for the measured device 6. That is, the calculation/display circuit 15 multiplies the digital data obtained by the A/D conversion circuit 14 by the sensitivity of the measurement system, calculates the voltage or the electrical field of each measured point on the measurement line of the measured device, and displays the voltage distribution or electrical field distribution on the measurement line of the measured device 6 in a time sequence using the data values or a waveform. In addition, the measurement data at each measurement point is displayed in a time series, that is, on a time axis, using the data values or a waveform.

Although one aspect has already been explained, the method of extracting the line-shaped voltage or electrical field of the measured device 6 will be explained referring to FIG. 3. The laser light input into the electrooptic element 4 has a line-shaped or elongated elliptic shape, and this light path is the schematically represented by the light path 18. As shown in FIG. 3, in the electrical field irradiated by the measured device 6, the laser beam transits only the line-shaped shaped part from the line-shaped electrical field 19-1 to electrical field 19-n of the measured device. It transits a different place in the electrooptic element 4 from the incident light path 18-1 to light path 18-n.

The electrical field 19 radiates the electrooptic element 4 from the measured device and the laser of the light path 18-1 transits the electrical field 19-1. Similarly, the light paths 18-2, 18-3, . . . , 18-n respectively transit electrical fields 19-2, 19-3, . . . , 19-n. The laser light of the light path 18-1 undergoes polarization change due to the electrical field 19-1, and similarly, light paths 18-2, 18-3, . . . , 18-n respectively undergo a polarization change due to the electrical fields 19-2, 19-3, . . . , 19-n.

Figure 4:
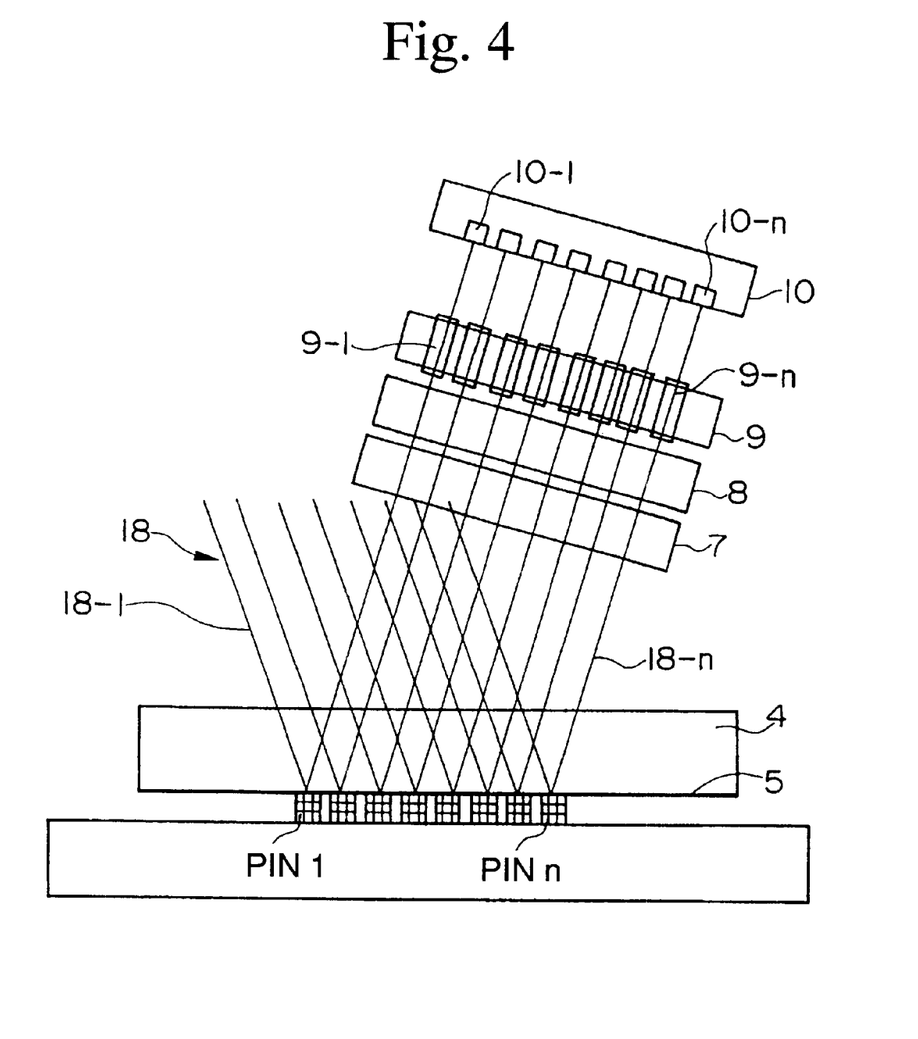
FIG. 4 is an explanatory diagram showing the structure of the optical system and the light receiving device when measuring the voltage distribution and the electrical field distribution of the measured device having a known structure.

Next, in the case that the structure of the measured device is already known, for example, when of a pin structure of an IC (dimensions, number of pins, and the like) is already known, one part of the optical system and the line sensors serving as a light receiving device in the semiconductor test apparatus can be structured as shown in FIG. 4. Specifically, the case will be explained wherein the measured device 6 is disposed so that n points (electrodes) from pin 1 to pin n are arranged in a line, and the voltage of each pint is measured simultaneously.

At the bottom surface of the electrooptic element 4, the distance from the light path 18-1 to light path 18-n is made to match the distance from the pin 1 to pin n of the measured device. The microlens array 9 has microlenses 9-1 to 9-n in which the light paths 18-1, 18-2, 18-n respectively transit microlenses 9-1 to 9-n arranged at intervals, and each of the light receiving surfaces on the line sensor 10 is formed such that each condensed laser beam is incident on each light receiving surface from the light receiving surface 10-1 to 10-n respectively at microlens 9-1 to microlens 9-n.

The microlens 9 and the line sensor 10 are formed and arranged such that the signals of each of the pins of the measured device 6 coincide one-to-one with each of the light receiving surfaces of the line sensor 10, so that the measurement signal of the electrical field or the voltage in pin 1 of the measured device 6 is received by the light receiving surface 10-1 of the line sensor 10, and similarly, the signals of pins 2, 3, . . . , n are respectively received by the light receiving surfaces 10-2, 10-3, . . . , 10-n.

In this manner, in the case that the electrical field or voltage in each of the pins of a measured device 6 having a known structure are measured, the numbers of microlenses of the microlens array and the light receiving surfaces of the line sensor are limited to n, which is the number of the pins of the measured device 6, and the structure of the microlens array and the line sensor can be simplified.

Figure 5:
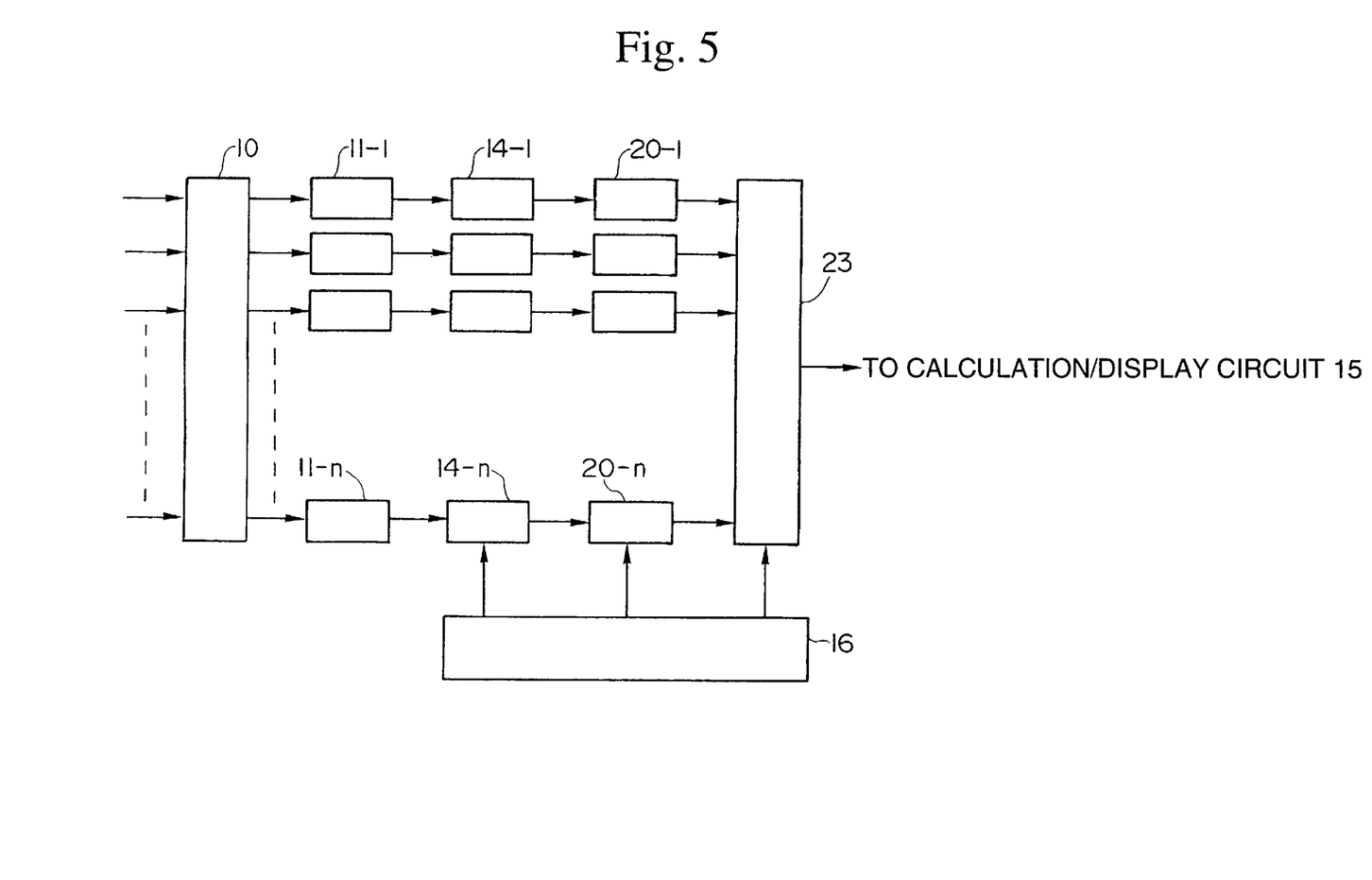
FIG. 5 is a block diagram of another structure of a signal processing device in the semiconductor test apparatus according to the embodiment of the present invention shown in FIG. 1.

The signal processing subsequent to the line sensor 10 will be explained referring to FIG. 5. FIG. 5 shows another structure of the signal processing device in the semiconductor test apparatus shown in FIG. 1. In this figure, the signal comprises n signal processing device amplifying circuits 11-1 to 11-n that amplify each of n output signals output from the line sensor 10, n A/D conversion circuits 14-1 to 14-n that A/D convert each of the output signals of the n amplifying circuits 11-1 to 11-n, n latch circuits 20-1 to 20-n that latch the n output signals of the A/D conversion circuits 14-1 to 14-n, and a selection circuit 23 that selects and inputs in sequence the outputs of the n latch circuits 20-1 to 20-n, and output the result to the calculation/display circuit 15.

In the structure described above, each of the n output signals output from the line sensor 10 are respectively amplified by the n amplifying circuits amplifying circuit 10-1 to amplifying circuit 10-n, and these amplified outputs are A/D converted simultaneously by A/D conversion circuits 14-1 to 14-n. In addition, the digital signals output from the A/D conversion circuits 14-1 to 14-n are simultaneously latched by the latch circuits 20-1 to 20-n, these latched signals are selected in sequence by the selection circuit 23, and output to the calculation/display circuit 15. The selection circuit 13 in the semiconductor test apparatus shown in FIG. 1 is a selection circuit for analog signals, and the selection circuit 23 shown in FIG. 5 is selection circuits for digital signals.

Figure 6:
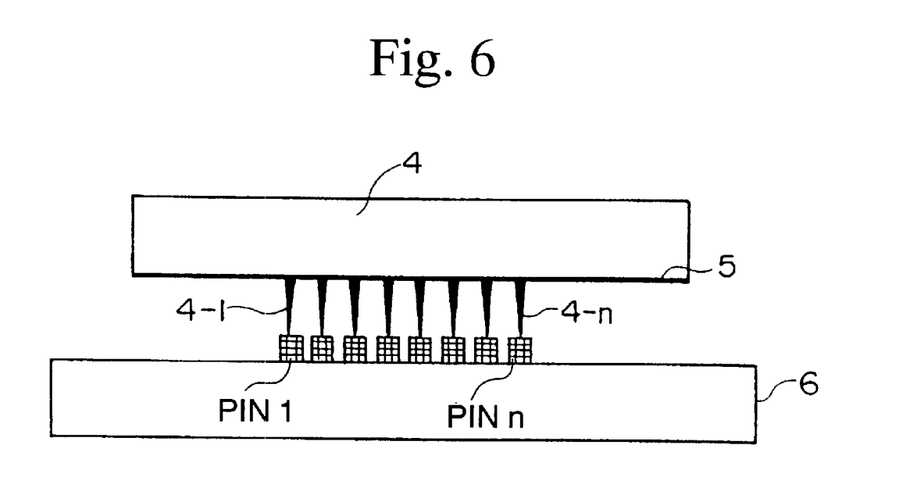
FIG. 6 is a drawing showing another example of the structure of the electrooptic element in the semiconductor test apparatus according to the embodiment of the present invention shown in FIG. 1.

As shown in FIG. 6, the electrooptic element 4 is structured such that the electrical field generated in the measured device 6 using the electrode is guided to the electrooptic element 4. In this example of the structure, n electrodes 4-1 to 4-n are formed in a line, and are respectively fixed at the reflection positions at the bordering surfaces between the bottom surface of the electrooptic element 4 and the reflection plate 5.

In addition, a magneto-optic element is used instead of the electrooptic element 4, and by detecting the magnetic field generated by the measured device 6, a one-dimensional or two-dimensional distribution of the magnetic field can be obtained.

In addition, a structure is possible wherein light path 18-1 to light path 18-n are generated by a plurality of curved mirrors instead of the one curved mirror 3, as shown in FIG. 1. Furthermore, a structure is possible wherein the light path 18-1 to light path 18-n are generated by a plurality of curved mirrors using a lens array instead of the condenser lens 2 and the curved mirror 3. In this case, these must be arranged on a straight line between the light source 1 and the electrooptic element 4.

As explained above, according to the first through tenth aspects of the invention, in a semiconductor test apparatus wherein a light beam emitted from a light source irradiates a measured part of a measured device via an electrooptic element arranged above the measured device, and the electrical field distribution or the voltage distribution in the measured part of the measured device is calculated by electrically detecting the change of state of the polarization of this reflected beam, a first aspect of the invention is characterized in comprising a first optical system wherein light emitted from the light source is shaped into a line-shaped light beam and irradiates a desired measurement line in the measured device via the electrooptic element, a second optical system that maintains as-is the shape of the line-shaped light beam reflected from the desired measurement line in the measured device after transiting the electrooptic element, a light receiving device that receives the line-shaped light beam emitted from the second optical system and converts and outputs for each of the measured points to an electrical signal depending on the strength of each light beam reflected at each of the measured points on the desired measurement line on the measured device, and a signal processing device that calculates the voltage or electrical field at each of the measured points of the measured device from the output signal of the light receiving device and calculates the electrical field distribution or the voltage distribution at the measured part of measured device, and thereby the voltage distribution or electrical field distribution in a measured device can be calculated in one-dimension or two-dimensions, and a reduction of the calculating time can be implemented.

For example, the voltage waveform of the pins of an IC arranged in one row can be measured simultaneously. Thereby, in the case of a conventional apparatus, for example, a plurality of sensors at a plurality of locations are necessary in order carry out the simultaneous measurement in the measured device, but this is unnecessary in the semiconductor test device according to the embodiment of the present invention, and in the present embodiment, measurement can be carried out with one semiconductor test apparatus.

In addition, according to the semiconductor test apparatus of the present embodiment, the voltage distribution and saturation condition of a propagation path of a microstrip array and the like can be measured in the propagation direction.

In addition, according to the semiconductor test apparatus of the present embodiment, the measurement time can be reduced by carrying out the measurement of a plurality of locations simultaneously. For example, the measurement time can be reduced to 1/20 by measuring 20 locations simultaneously, and the timing adjusting time interval of the semiconductor test apparatus can be reduced from 100 minutes to 5 minutes.

Furthermore, according to the semiconductor test apparatus of the present embodiment, the two-dimensional voltage (electrical field) distribution can be easily measured by relatively moving (sweeping) the electrooptic element in the measurement direction of the measured device 6. In the case of using a magneto-optic element instead of an electrooptic element as well, similarly, a two-dimensional current (magnetic field) distribution can be simply measured by relatively moving (sweeping) the magneto-optic element in a direction perpendicular to the direction of the measurement of the measured device 6.

According to the first through tenth aspects of the invention, in a semiconductor test apparatus wherein a light beam emitted from a light source irradiates a measured part of a measured device via an electrooptic element arranged above the measured device, and the electrical field distribution or the voltage distribution in the measured part of the measured device is calculated by electrically detecting the change of state of the polarization of this reflected beam, a first aspect of the invention is characterized in comprising a first optical system wherein light emitted from the light source is shaped into a line-shaped light beam and irradiates a desired measurement line in the measured device via the electrooptic element, a second optical system that maintains as-is the shape of the line-shaped light beam reflected from the desired measurement line in the measured device after transiting the electrooptic element, a light receiving device that receives the line-shaped light beam emitted from the second optical system and converts and outputs for each of the measured points to an electrical signal depending on the strength of each light beam reflected at each of the measured points on the desired measurement line on the measured device, and a signal processing device that calculates the voltage or electrical field at each of the measured points of the measured device from the output signal of the light receiving device and calculates the electrical field distribution or the voltage distribution at the measured part of measured device, and thereby the voltage distribution or electrical field distribution in a measured device can be calculated in one-dimension or two-dimensions, and a reduction of the calculating time can be implemented.

In addition, according to the eleventh aspect of the invention, in the semiconductor test circuit according to any of the first through ninth aspects, the magnetic field distribution and the current distribution in the desired measured part of the measured device are calculated using a magneto-optic element instead of the electrooptic element, and thereby the one-dimensional or two-dimensional voltage distribution or electrical field distribution in a measured device can be calculated, and a reduction of the calculating time can be implemented.

What is claimed is:
1. A semiconductor test apparatus in which a light beam emitted from a light source irradiates a measured part of a measured device via an electrooptic element arranged above the measured device and the electrical field distribution or the voltage distribution in the measured part of said measured device is calculated by electrically detecting the change in the state of the polarization of this reflected beam, comprising:

a first optical system wherein light emitted from said light source is shaped into a line-shaped light beam and irradiates a desired measurement line on said measured device via said electrooptic element, a second optical system that maintains as-is the shape of the line-shaped light beam reflected from the desired measurement line on said measured device after transiting said electrooptic element, and modulates the change in polarization of said line-shaped light beam to a change in the intensity of the light, a light receiving device that receives the line-shaped light beam emitted from said second optical system and converts the light beam at each measured point to an electrical signal depending on the strength of each light beam reflected at each measured point on the desired measurement line on the measured device and outputs the result, and a signal processing device that calculates the voltage or electrical field at each of the measured points on the measured device from the output signal of said light receiving device and calculates the electrical field distribution or the voltage distribution at the measured part on the measured device.

2. A semiconductor test apparatus according to claim 1, wherein the signal processing device comprises:

a sample holding circuit that holds samples of the output signal of said light receiving device simultaneously for each of the measured points of said measured device, a selection circuit that selects in sequence the samples of the signals held by said sample holding circuit, an A/D conversion circuit that A/D converts the analog signal selected by the selecting circuit, and a timing generation circuit that outputs a timing signal that controls the timing of the operation of said sample holding circuit, the selection circuit, and the A/D conversion circuit.

3. A semiconductor test apparatus according to claim 2, wherein said light source is driven so as to emit light continuously, and at each timing wherein the A/D conversion of the signal representing the electrical field or voltage at each of the measured points of the measured part on said measured device irradiated by said line-shaped light beam has completed, said sample holding circuit holds samples of the signals representing the electrical field or voltage at each of the measured points.

4. A semiconductor test apparatus according to claim 3, wherein the timing is such that the A/D conversion rate of said A/D converting device ADDed to the number of signals output from said light receiving device becomes equal to the sample rate of said sample holding circuit, and said light source is driven so as to emit pulsed light at a timing in synchronism with a reference signal that determines the measurement timing, and at the same time, said sample holding circuit holds samples of the signals that represent the electrical field or the voltage of each of the measured points at the measured parts of said measured device irradiated by said line-shaped light beam at a timing in synchronism with the light emission timing.

5. A semiconductor test apparatus according to claim 1, wherein the first optical system comprises:

a condenser lens that condenses the light emitted from the light source, and a curved mirror that shapes the light beam condensed by said condenser lens into a line-shaped light beam and irradiates a desired measurement line on said measured device via said electrooptic element.

6. A semiconductor test apparatus according to claim 1, wherein the second optical system comprises:

a reflecting plate that is arranged on the lower surface of said electrooptic element, and reflects the line-shaped light beam irradiated by said first optical system, a wavelength plate that converts the line-shaped light beam reflected by said reflecting plate to line-shaped polarized light, an analyzer that converts an amount of polarization of the line-shaped light beam that has transited said wavelength plate to an amount of amplitude, and a microlens array that condenses each of the reflected light beams corresponding to each of the measured points on the line-shaped light beam of said measured device that has transited the analyzer on each of the light receiving surfaces of said light receiving device corresponding to each of said reflected light beams.

7. A semiconductor test apparatus according to claim 1, wherein the semiconductor test apparatus further comprises a calculation/display device, and this calculation/display device calculates and displays the electrical field or the voltage value based on the output signals of said A/D converting circuit.

8. A semiconductor test apparatus according to claim 7, wherein said signal processing means calculates a plurality of times the electrical field distribution or voltage distribution on the measurement line of said measured device obtained based on the amplitude information of the reflected beam of the desired line-shaped light beam that irradiates the measured part of said measured device, and the calculation/display device displays on a time axis the electrical field distribution or voltage distribution on the measurement line of said measured device that have been calculated said plurality of times.

9. A semiconductor test apparatus according to claim 1, wherein the calculation/display device displays the electrical distribution or the voltage distribution on the measurement line of said measured device that has been obtained based on the amplitude information of the reflected beam of the line-shaped light beam irradiating said measured device via said electrooptic element.

10. A semiconductor test circuit according to claim 1, wherein said signal processing means comprises:

a plurality of amplifying circuits that amplify each of the plurality of output signals output from said light receiving devices, a plurality of A/D conversion circuits that A/D convert each of the output signals of the plurality of amplifying circuits, a plurality of latch circuits that latch the output signals of the plurality of A/D conversion circuits, and a selection circuit that selects in sequence each of the outputs of said plurality of latch circuits.

11. A semiconductor test circuit according to claim 1, a magnetic field distribution or a current distribution in the desired measured part of said measured device is calculated using a magneto-optic element instead of said electrooptic element.

* * * * *